(12) United States Patent
Whewell

(10) Patent No.: US 7,300,957 B1
(45) Date of Patent: Nov. 27, 2007

(54) SKIN CARE COMPOSITIONS

(76) Inventor: Christopher J. Whewell, 6020 Tonkowa Trail, Georgetown, TX (US) 78628

( * ) Notice: Subject to any disclaimer, the term of this patent is extended or adjusted under 35 U.S.C. 154(b) by 0 days.

(21) Appl. No.: 11/524,556

(22) Filed: Sep. 21, 2006

Related U.S. Application Data

(60) Provisional application No. 60/814,147, filed on Jun. 16, 2006.

(51) Int. Cl.
*A61K 31/225* (2006.01)

(52) U.S. Cl. .................. 514/547; 514/558; 514/859

(58) Field of Classification Search ........... 514/547, 514/558, 859
See application file for complete search history.

(56) References Cited

U.S. PATENT DOCUMENTS

| | | | |
|---|---|---|---|
| 4,070,523 A | 1/1978 | Blum et al. | 428/352 |
| 4,542,052 A | 9/1985 | Shadbolt et al. | 428/40 |
| 4,661,519 A * | 4/1987 | Shiga et al. | 514/547 |

OTHER PUBLICATIONS

Bougault, J.; Schuster, G. The Composition of cacao butter. Remarks on the not e by Hilditch reporting the partial saponification of mixed azelaic glycerides. Bull. Sec. Chim. (1934), 1, 1416-1419.*

* cited by examiner

*Primary Examiner*—Michael G. Hartley
*Assistant Examiner*—Jagadishwar Samala
(74) *Attorney, Agent, or Firm*—Chris Whewell

(57) ABSTRACT

Provided are compositions which are suitable for topical application to human skin for cleansing and anti-microbial properties. In one preferred embodiment, the compositions include a glyceryl monoazelate ester. In another embodiment, the compositions include a glyceryl monoazelate monolaurate ester. It is postulated that bacteria on the skin cleave the ester linkage of a compound according to the invention that is applied to the skin, which causes liberation of the acid moiety from the ester, which acid moiety then inhibits or kills the bacterium. Compositions according to the invention may comprise skin creams, soaps, shampoos and lotions, and are especially effective in treating acne and acne-like skin ebullitions. The glyceryl portion of the molecules is believed to facilitate penetration of the ester into the skin.

6 Claims, No Drawings

SKIN CARE COMPOSITIONS

CROSS-REFERENCES TO RELATED APPLICATIONS

This application claims the benefit of U.S. Provisional Application Ser. No. 60/814,147 filed Jun. 16, 2006, the entire contents of which are herein incorporated by reference.

TECHNICAL FIELD

This invention relates generally to compositions of matter which can be applied to mammalian skin and hair, including that of humans, bovine, equestria and canines. More particularly, it relates to personal care compositions useful in managing the appearance of hair and skin, and are well-suited to promoting health of human skin.

BACKGROUND

Various compositions of matter are known to be usefully applied to human skin for a variety of purposes, including anti-acne, anti-wrinkle, anti-bacterial, anti-carbuncle, pediculicide, etc. In many cases, such compositions include one or more esters as part of their formulations. Often, so-called skin creams, vanishing creams, and the like comprise emulsions, in which one or more active ingredients are present in any amount between about 0.001% by weight to about 50% by weight or more, as in the case of concentrates from which emulsions may be prepared. Workers in the prior art have provided a large number of stable skin cream emulsions, many of which are described in expired patents, or patents which are in-force, but not claimed therein. Such prior art patents include, without limitation U.S. Pat. Nos. 6,989,195; 6,903,134; 6,638,621; 6,599,513; 6,596,287; 6,582,710; 6,573,299; 6,552,050; 6,531,117; 6,492,326; 6,464,992; 6,444,647; 6,428,779; 6,403,619; 6,372,234; 6,337,065; 6,284,802; 6,261,575; 6,180,133; 5,876,737; 5,821,237; and 5,126,327 all of which are herein incorporated fully by reference thereto. Conventional skin cream emulsions are thus well-known in the art.

SUMMARY OF THE INVENTION

The present inventions provides compositions of matter useful for topical application to human skin. Compositions according to the invention comprise at least one ester compound having a structure selected from the group consisting of:

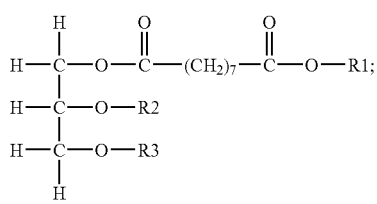

(I)

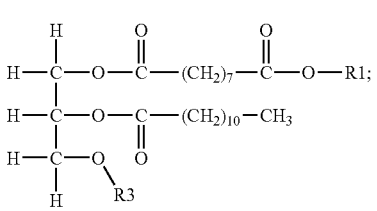

(II)

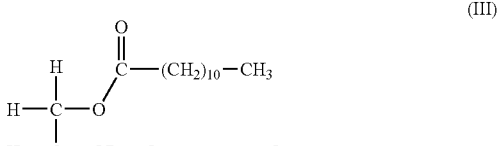

(III)

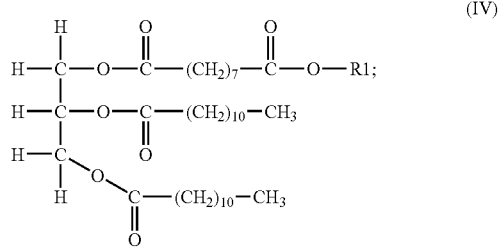

(IV)

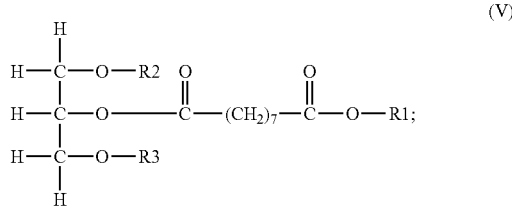

(V)

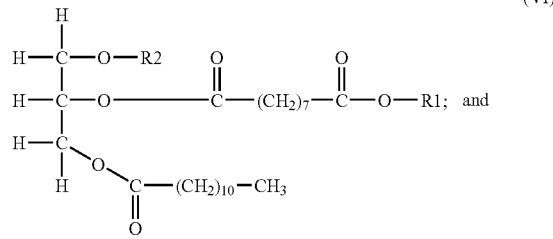

(VI)

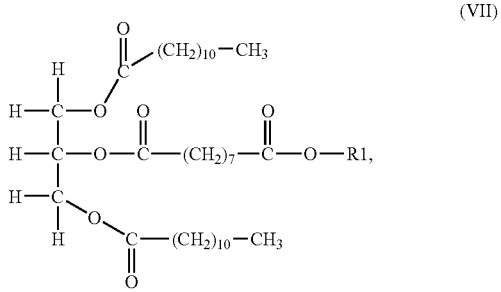

(VII)

wherein R1, in each occurrence, is selected from the group consisting of: hydrogen, a metal cation, a substituted or unsubstituted ammonium ion, any C1-C18 hydrocarbyl group, and a glyceryl group having the structure:

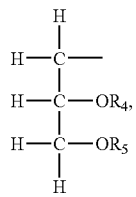

in which R4 and R5 are in each occurrence independently selected from the group consisting of: hydrogen and any C1-C18 hydrocarbyl group; and R2 and R3 are each, in each occurrence, independently selected from the group consisting of: hydrogen, any C1-C18 hydrocarbyl group, and a glyceryl group having the structure:

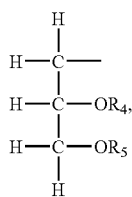

in which R4 and R5 are in each occurrence independently selected from the group consisting of: hydrogen and any C1-C18 hydrocarbyl group. The invention also provides compositions per the above in which adjacent R2 and R3 groups, when present, collectively comprise a bridging C1 to C4 alkylene group. The invention also provides methods for treating human skin by applying the compositions to the skin.

DETAILED DESCRIPTION

The present invention concerns the incorporation of one or more novel esters as described herein into emulsions or creams which are suitable for application to human hair and skin, wherein the one or more novel esters are present in any amount between about 0.01% to about 20% or more by weight based on the total weight of the finished emulsion, creme, paste, shampoo, or other formulation.

The novel esters useful as ingredients in a skin-care composition according to the present invention include: lauryl phytate; glyceryl phytate; inosityl laureates; lauryl azelate; glyceryl azelates, inosityl azelates. Thus, the acids from which esters according to the invention may be derived include, without limitation: phytic acid, lauric acid, and azelaic acid, and the alcohols from which esters according to the invention may be derived include, without limitation: lauryl alcohol, glycerine, inositol.

There are in general three preferable methods for producing esters useful according to the present invention. In one embodiment, glycerine is directly esterified with the necessary carboxylic acid, using means well known in the art of esterification. This includes heating a mixture of glycerine and a base catalyst, present in an effective catalytic amount, to a temperature in the range of between about 80 degrees C. and 180 degrees C., and adding a desired amount of the selected carboxylic acid, one of its salts, such as an alkali metal salt of the carboxylic acid, either the mono- or di-acid salt, as appropriate, depending upon the acid selected. (Alternatively, acyl halides of the acids may be used, but these are expensive and require great skill to work with.) After refluxing with stirring for a few hours, for any amount of time in the range of between about 1 hour to 18 hours, during which liberated water is collected in a Dean-Stark trap or side-arm condenser and removed to drive the reaction towards completion. In one preferred embodiment, an excess of glycerine is employed, in order to drive the reaction to completion and to ensure a large relative proportion of mono-ester formation. For example, in the case where lauric acid is added to glycerine under reflux or near boiling in the presence of a base catalyst, a ten-fold excess of glycerine may be used, and the reaction product mixture, after cooling, may be diluted with a large volume of water, into which the un-reacted glycerine is dissolved and separated using a separatory funnel or by decantation from the crude ester and unreacted acid. After rinsing the crude ester several times with an aqueous solution of sodium bicarbonate, traces of residual base catalyst are effectively removed, and the crude ester may be washed with several aliquots of distilled water to yield a clean crude ester product, which may be further worked up and purified by vacuum distillation or molecular distillation. In an alternate embodiment of this method, an ester of the desired carboxylic acid comprising a C1-C18 alcohol substrate may be used in place of the carboxylic acid, such as methyl esters. In such embodiment, methanol, and not water, is liberated as the reaction proceeds.

Another general method of producing an ester useful in accordance with the present invention is according to the teachings of Yu et al. in *Bull. Korean Chem. Soc.* 2003, Vol. 24, No. 8, which is fully incorporated herein by reference thereto. In such embodiment, 1,3-dioxolane-4-methanol, 2,2-dimethyl, a.k.a., the glyceryl ketal of acetone, is employed as a substrate for esterification with the selected acid. In one embodiment, the methyl ester of lauric acid and the glyceryl ketal of acetone are employed as raw materials and the procedure therein followed to yield essentially pure glyceryl monolaurate, itself a powerful antimicrobial agent which is useful as a component in a composition according to the present invention.

In yet another general method useful for providing a glyceryl azelate ester useful in accordance with the present invention, an glycerine tri-ester oil may be trans-esterified, by heating the oil chosen in the presence of a base or acid catalyst and adding the desired carboxylic acid, or its acyl or ester derivative. For example, beef tallow, soybean oil, coconut oil, peanut oil, or any animal-derived oils or plant-derived oils which are predominantly comprised of triesters of glycerine may be heated to a temperature in the range of between about 80 degrees C. and 180 degrees C. in the presence of an effective catalytic amount of acid or base catalyst, to which is added a selected carboxylic acid or ester thereof, as is known in the art.

The selected carboxylic acid or esters thereof which are suitable for use as raw materials in the foregoing preparative methods for providing an additive for a personal care composition (to be applied to hair or skin) according to the invention include without limitation: azelaic acid, mono-alkyl azelaic acid esters derived from any C1 to C18 alcohol (such as monomethyl azelate, monomethyl azelate, monopropyl azelate, etc.); di-alkyl azelaic acid esters derived from any C1 to C18 alcohol, lauric acid (such as dimethyl azelate, dimethyl azelate, dipropyl azelate, etc.), mono-alkyl lauric acid esters derived from any C1 to C18 alcohol (such as methyl laurate, ethyl laurate, propyl laurate, etc.), and all forms of phytic acid, including any of its various known salts. In one embodiment, azelaic acid and its lower C1 to C6 alkyl esters are especially preferred in providing mixed esters of azelaic acid and lauric acid with glycerine. Azelaic acid has the structure:

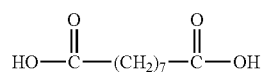

Thus, an ester useful as a component in a skin-care or hair-care composition according to preferred embodiments of the present invention comprises one or more compounds having a structure selected from the group consisting of:

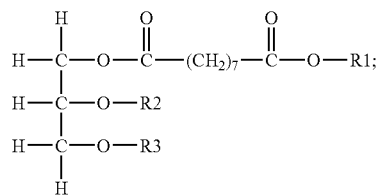
(I)

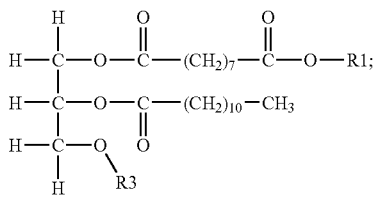
(II)

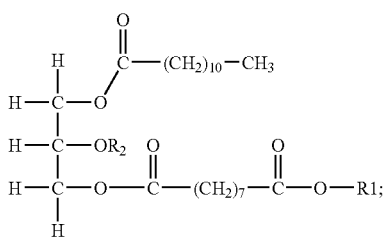
(III)

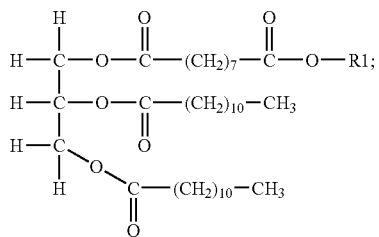
(IV)

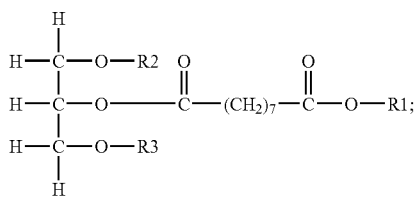
(V)

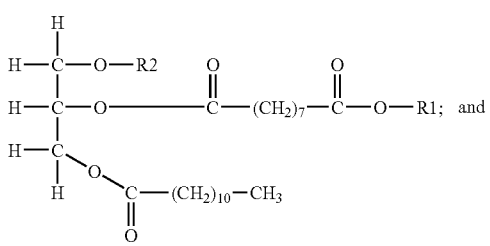
(VI)

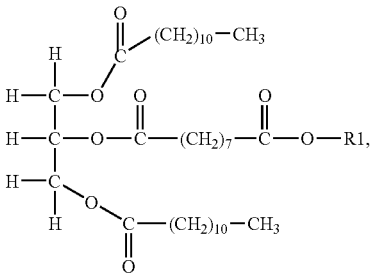
(VII)

wherein R1, in each occurrence, is selected from the group consisting of: hydrogen, a metal cation, a substituted or unsubstituted ammonium ion, any C1-C18 hydrocarbyl group, and a glyceryl group having the structure:

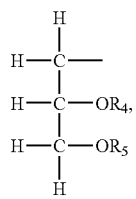

in which R4 and R5 are in each occurrence independently selected from the group consisting of: hydrogen and any C1-C18 hydrocarbyl group; and R2 and R3 are each, in each occurrence, independently selected from the group consisting of: hydrogen, any C1-C18 hydrocarbyl group, and a glyceryl group having the structure:

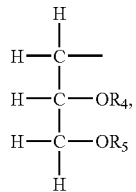

in which R4 and R5 are in each occurrence independently selected from the group consisting of: hydrogen and any C1-C18 hydrocarbyl group. Within this definition the groups R2 and R3 may also collectively comprise any bridging C1-C4 alkylene group, as in the case of structure (I) wherein R2 and R3 comprise the carbon atoms of an ethylene group that links the two oxygen atoms of the carbon atoms to which R2 and R3 are attached. R2 and R3 may be replaced by a single methylene group, any propylene group, or any butylene group. R2 and R3 may also collectively comprise a carbonyl group, such as in the case when glycerine carbonate is used as a raw material in accordance with Example VII, in which it is treated with a di-alkyl azelate to produce an ester according to the invention.

The glyceryl azelates are powerful anti-microbial agents for skin. They relieve acne quickly. They are also environmentally-friendly. The mixed ester of glyceryl lauryl azelate of structure (III) is especially powerful in treating acne.

The term "hydrocarbyl", as used in this specification and the claims appended hereto, refers to a hydrocarbon group having a carbon atom directly attached to the remainder of the molecule and having predominantly hydrocarbon character. Examples of hydrocarbyl substituents or groups within this definition include: (1) hydrocarbon substituents, that is, aliphatic (e.g., alkyl or alkenyl, including straight-chain or branched), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical); (2) substituted hydrocarbon substituents, that is, substituents containing non-hydrocarbon groups which, in the context of this invention, do not alter the predominantly hydrocarbon substituent (e.g., halo (especially chloro and fluoro), hydroxy, carboxy (including C1-C24 carboxylate groups), alkoxy, mercapto, alkylmercapto, nitro, nitroso, and sulfoxy); (3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents such as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in a hydrocarbyl group, with methyl and ethyl groups comprising preferred embodiments of hydrocarbyl groups.

It is known in the art of esterification of glycerine and transesterification of glycerine that it is rare for the product of such reactions to comprise a single molecule as a reaction product. Rather, mixtures of esters are typically obtained owing to the presence of several complex and competing reaction equilibria. Alteration of such variables as reaction time; temperature; reactant and product composition and concentration; pH; presence, nature and identity of catalyst(s) present; and pressure will tend to shift the positions of the various competing equilibria, and typically complex mixtures result even from the addition of lauric acid to heated tallow in the presence of a base or acid, since acid catalysts, including without limitation sulfonic acids and carboxylic acids, are also well known to also catalyze esterifications and transesterifications. Thus, the crude mixture resulting from a reaction directed at producing one or more materials described in formula (I) through (VII) above will typically comprise a multi-component mixture of glyceryl azelates. For purposes of this specification and the claims appended hereto, the words "glyceryl azelate" includes any compound described by formulae (I) through (VII) and the text above.

It has been seen that in the foregoing description, the appendage R1 is present on a carboxyl function of the glyceryl azelate ester. While R1 may represent many alkyl groups, or alkoxy groups; however, R1 may also comprise a cationic species. Within this context, R1 may comprise any alkali metal, alkaline earth metal, Group III cations (boron, aluminum, et al.) or transition metal cation. Additional suitable cationic species include ammonium cations, mono-alkylammonium cations, di-alkylammonium cations, tri-alkylammonium cations, and quaternaryalkylammonium cations. For alkylated ammonium cations, the alkyl group(s) may comprise any number of carbon atoms from about 1 to about 24. When the cationic species selected is multivalent, charge balance naturally needs to be maintained and in the case of a tri-positive cation such as aluminum, only one aluminum cation is required to be present for each three anionic species comprising a glyceryl azelate salt according to the invention. This is one especially useful employment to the compounds of the invention, since, when the structure of material is that of a glyceryl azelate ester in any of the formulae above in which R1 is an aluminum or zirconium cation, the compositions of the invention are useful as additives in anti-perspirant compositions, owing to their unique property of being soluble in both oils and in aqueous systems. This may in some cases enable deeper penetration into the middle layers of the skin than many other products, to put more active ingredient at the site of unwanted and high microbe populations.

Selection of the desired cation can be made after the hydrolysis step when producing a composition of the invention using the glyceryl ketal of acetone and a di-ester of azelaic acid. Alternatively, to illustrate another principle useful in accordance with producing compounds according to the invention, monosodium azelate may be esterified with methanol to yield monosodium monomethyl azelate which can be added in powder form to a heated and stirred quantity of the acetone ketal of glycerine, but the yield is likely lower when using this approach versus post neutralization of the acid form of glyceryl azelate that is made using azelate di-esters as a reactant with the acetone ketal of glycerine. However, the hydrolysis step involving de-protection of the ketal can be performed with the slow addition of a weakly acidic substance comprising the desired cation over time, such as lithium bicarbonate, aluminum bicarbonate, zinc carbonate, ammonia, diethylamine, alkanolamines, dimethylaminoethanol, alkanolamines, etc. so that the cation is incorporated during the hydrolysis, thus minimizing the propensity for precipitates to form when long alkyl groups are present on R2 and R3.

Alternatively, anionic glyceryl azelate species may be formed in situ, upon mixing the acid form wherein R1 is hydrogen in formula (I) with the other ingredients of a cream, emulsion, shampoo or other skin care formulation, by simple replacement reactions.

Only effective amounts of glyceryl azelate are needed to prevent or treat skin conditions such as acne, so generally topical application to exposed or affected skin sites is accomplished in association with a carrier, and particularly one in which the active ingredient is soluble per se or is effectively solubilized (e.g., as a solution, emulsion or microemulsion). It is necessary that the carrier be inert in the sense of not bringing about a deactivation or de-esterification of the glyceryl azelate or glyceryl azelates present in the formulation, and in the sense of not bringing about any adverse effect on the skin areas to which it is applied.

Suitable carriers include water, alcohols, oils and the like, chosen for their ability to dissolve or disperse the active ingredients at concentrations of active ingredients most suitable for use in the therapeutic treatment. Generally, even low concentrations of active ingredients in a carrier will be suitable, requiring only that more frequent topical application be resorted to. As a practical matter, however, to avoid the need for repeated application, it is desirable that the topically applied composition be formulated to contain at least about 0.25% to about 5% by weight, more preferably from about 1% to about 3% by weight, glyceryl azelate, glyceryl azelates or a derivative thereof, and accordingly, carriers will be chosen which can solubilize or disperse the active ingredients at such concentrations. In one embodiment, glyceryl azelate esters are present in a composition according to the invention in any amount between about 0.01% to about 30% by weight based on the total weight of the finished emulsion containing the ester. One efficacious embodiment contains about 2% by weight total glyceryl azelates content.

While the carrier for glyceryl azelate can consist of a relatively simple solvent or dispersant such as oils, it is generally preferred that the carrier comprise a composition more conducive to topical application, and particularly one which will form a film or layer on the skin to which it is applied so as to localize the application and provide some resistance to perspiration and/or one which aids in percutaneous delivery and penetration of the active ingredients into lipid layers. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Such compositions may be referred to as dermatologically acceptable carriers. Most preferred for skin are those carriers which are fat-soluble, i.e., those which can effectively penetrate skin layers and deliver the active glyceryl azelate or glyceryl azelates to the lipid-rich layers of the skin. In addition, an ester according to the invention may be applied using a time-release patch, as are used in hormone delivery, nicotine patches, anti-acne patches, and the like. Cremes, aqueous solutions, pastes, powders, etc. are al suitable delivery vehicles for an ester described herein to the human body.

Thus, the glyceryl azelate esters of the present invention may be used in a wide range of personal care compositions (compositions suitable to be applied to either hair or skin or both), as an additive at levels ranging from 1% to 60% by weight based on the total weight of the personal care composition. In addition, the glyceryl azelate esters of the present invention may be blended with other surfactants and materials which are used in personal care products at glyceryl azelate ester levels ranging up to about 60% by weight. To the extent that other surfactants may be used in combination with the glyceryl azelate esters of the present invention in forming binary active systems, ternary active systems etc., the glyceryl azelate ester may comprise the majority of an anti-microbial additive system or it may comprise less than the majority of the anti-microbial additive system in which case it is referred to as the secondary additive. Surfactants and materials which may be used in combination with the glyceryl azelate esters in forming personal care compositions according to the invention include without limitation: amphoteric/zwitterionic surfactants; anionic surfactants; nonionic surfactants; cationic surfactants; and optional ingredients, including those described below.

Amphoteric surfactants suitable for inclusion in a personal care composition along with a glyceryl azelate according to the present invention can broadly be described as surface active agents containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants suitable for inclusion in a personal care composition along with a glyceryl azelate according to the present invention can be described as surface active agents having a positive and negative charge in the same molecule which molecule is zwitterionic at all pH's. Zwitterionic surfactants can perhaps be best illustrated by the betaines and the sultaines. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate.

Examples of amphoteric and zwitterionic surfactants suitable for inclusion in a personal care composition along with a glyceryl azelate according to the present invention include the alkali metal, alkaline earth metal, ammonium or substituted ammonium salts of alkyl amphocarboxyglycinates and alkylamphocarboxypropionates, alkyl amphodipropionates, alkyl monoacetate, alkyl diacetates, alkylamphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates.

Anionic surfactants suitable for inclusion in a personal care composition along with a glyceryl azelate according to the present invention are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants. Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group. Other anionic surfactants that can be mentioned include alkylsulfosuccinates, alkyl ethersulfosuccinates, olefin sulfonates, alkyl sarcosinates, alkyl monoglyceride sulfates and ether sulfates, alkyl ether carboxylates, paraffinic sulfonates, mono and di-alkyl phosphate esters and ethoxylated derivatives, acyl methyl taurates, fatty acid soaps, collagen hydrosylate derivatives, sulfoacetates, acyl lactates, aryloxide disulfonates, sulfosucinamides, naphthalene-formaldehyde condensates and the like. Aryl groups generally include one and two rings, alkyl generally includes from 8 to 22 carbon atoms and the ether groups generally range from 1 to 9 moles of ethylene oxide (EO) and/or propylene oxide (PO), preferably EO. Specific anionic surfactants which may be selected include linear alkyl benzene sulfonates such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof.

Nonionic surfactants may also be used in combination with the glyceryl azelate esters of the present invention in a personal care or skin-care composition. The nonionic surfactant (s) is not generally critical and may be any of the known nonionic surfactants which are generally selected on the basis of compatibility, effectiveness and economy. Examples of useful nonionic surfactants include condensates of ethylene oxide with a hydrophobic moiety which has an average hydrophilic lipolytic balance (HLB) between about 8 to about 16, and preferably between about 10 and about 12.5. The surfactants include the ethoxylated primary or secondary aliphatic alcohols having from about 8 to about 24 carbon atoms, in either straight or branch chain configuration, with from about 2 to about 40, and preferably between about 2 and about 9 moles of ethylene oxide per mole of alcohol. Other suitable nonionic surfactants include the condensation products of from about 6 to about 12 carbon atoms alkyl phenols with about 3 to about 30, and preferably between about 5 to about 14 moles of ethylene oxide.

Many cationic surfactants are known in the art and almost any cationic surfactant having at least one long chain alkyl group of about 10 to 24 carbon atoms is suitable for optional use as a component in a final formulation which includes a glyceryl azelate according to the present invention.

Other optional ingredients or additives which may be used in combination with glyceryl azelate esters in formulating personal care compositions according to the present invention include pH adjusting chemicals, for example, loweralkanolamines such as monoethanolamine (MEA) and triethanolamine (TEA). Sodium hydroxide solutions may also be utilized as an alkaline pH adjusting agent. The pH adjusting chemicals function to neutralize acidic materials that may be present. Mixtures of more than one pH adjusting chemical can also be utilized.

Phase regulants (well known liquid detergent technology) may also be optionally used in the present invention. These can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Detergent hydrotropes may also be included. Examples of detergent hydrotropes include salts of alkylarylsulfonates having up to 3 carbon atoms in the alkyl group e.g., sodium, potassium, ammonium, and ethanolamine salts of xylene, toluene, ethylbenzene, cumene, and isopropylbenzenesulfonic acids.

Other optional supplemental additives include de-foamers such as high molecular weight aliphatic acids, especially saturated fatty acids and soaps derived from them, dyes and perfumes; fluorescent agents or optical brighteners; suspension stabilizing agents and soil release promoters such as copolymers of polyethylene terephthalate and polyoxyethylene terephthalate; antioxidants; softening agents and antistatic agents; photo activators and preservatives; polyacids, suds regulators, opacifiers, bacteriacide, and the like. Suds regulants can illustrated by alkylated polysiloxanes and opacifiers can be illustrated by polystyrene; bactericide can be illustrated by butylated hydroxytoluene.

Although not required, an inorganic or organic builder may optionally be added in small amounts to a final composition according to the invention. Examples of inorganic builders include water-soluble alkali metal carbonates, bicarbonates, silicates and crystalline and amorphous alumino-silicates. Examples of organic builders include the alkali metal, alkaline metal, ammonium and substituted ammonium polyacetates, carboxylates, polycarboxylates, polyacetyl carboxylates and polyhydroxy sulfonates. One example of a commonly used builder is sodium citrate.

The optional ingredients and optional surfactants can be added to the glyceryl azelate ester before, during or after formulation of the skin care or personal care formulation. In addition, blends of the glyceryl azelate ester in combination with these optional ingredients and surfactants can be made directly for sale or for compounding to meet the needs of the user.

Thus, the glyceryl azelate esters of the present invention are useful in formulations which contain materials typically used by and known to those skilled in the art as being useful in formulating soap products, skin-care compositions, shampoos and other cleansing products, particularly, but not limited, to personal care cleansers. For purposes of this invention, the words "material known to those skilled in the art as being useful in formulating soaps, detergents, and the like" means one or more of the materials selected from the group consisting of fatty acids, alkyl sulfates, ethanolamines, amine oxides, alkali carbonates, water, ethanol, isopropanol, pine oil, sodium chloride, sodium silicate, polymers, alcohol alkoxylates, zeolites, perborate salts, alkali sulfates, enzymes, hydrotropes, dyes, fragrances, preservatives, brighteners, builders, polyacrylates, essential oils, alkali hydroxides, ether sulfates, alkylphenol ethoxylates, fatty acid amides, alpha olefin sulfonates, paraffin sulfonates, betaines, chelating agents, tallowamine ethoxylates, polyetheramine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonate diphenyl oxide, and water soluble alkylbenzene sulfonates or alkyltoluene sulfonates, as the use of such in formulating soaps, detergents, and the cleansing-like products are known in the art.

In one embodiment, the glyceryl azelate esters of the present invention may be present in facial and body cleansing compositions. These cleansing compositions may also comprise a fatty acid soap together with other non-soap surfactants, such as mild synthetic surfactants. Body and facial cleaning compositions may also generally include a moisturizer or emollient and polymeric skin feel and mildness aids. The compositions may further optionally include thickeners (e.g., magnesium aluminum silicate, carbopol), conditioners, water soluble polymers (e.g., carboxymethylcellulose), dyes, hydrotropes brighteners, perfumes and germicides.

In another embodiment, the glyceryl azelate esters of the present invention may be present in a shampoo. The shampoo composition may also comprise one or more other surfactants, optionally a compound considered useful for treating dandruff, such as selenium sulfide, a suspending agent, an amide, nonionic polymer material for aiding in dispersing particles, nonvolatile silicone fluid, and a variety of other nonessential components suitable for rendering the composition more formulatable, such as preservatives, viscosity modifiers, pH adjusting chemicals, perfumes, and dyes.

In still another embodiment, the glyceryl azelate esters of the present invention may be present in a light duty liquid detergent composition. The light duty liquid detergent composition may further include one or more other surfactants, opacifiers (e.g. ethylene glycol di-stearate), thickeners (e.g. guar gum), antimicrobial agents, anti-tarnish agents, heavy metal chelators (e.g. EDTA), perfumes and dyes.

In a further embodiment, the glyceryl azelate esters of the present invention may be present in a heavy duty liquid detergent composition. The heavy duty liquid detergent composition may also include one or more other surfactants, an electrolyte (i.e. water soluble salt), enzymes with or without stabilizers such as calcium ion, boric acid, propylene glycol and/or short chain carboxylic acids, and conventional alkaline detergency builders.

In yet another embodiment, the glyceryl azelate esters of the invention may be present in a conditioner composition that comprises alkylamine compounds.

In a different embodiment, the glyceryl azelate esters of the present invention may be present in a cosmetic composition, such as lipstick, and including lip balms. The cosmetic composition may further include at least one polymer thickening agent, one or more chemical preservatives or water activity depressants to prevent microbial spoilage, a sun-screening agent such as p-aminobenzoic acid, cinnamic acid derivatives, and a vehicle. The vehicle can include any diluent, dispersant or carrier useful in ensuring an even distribution of the composition when applied to skin and may include water, an emollient such as an alcohol or oil, a propellant for example, trichloromethane, carbon dioxide or nitrous oxide, a humectant, and a powder such as chalk, talc, and starch.

The examples which now follow should be considered exemplary of the present invention, and not delimitive thereof in any way.

EXAMPLE I

Glyceryl Azelates Concentrate

One mole (137 grams) of dry 2,2-dimethyl-1,3-dioxolane-4-methanol (97%, Alfa Aesar) and two grams of powdered zinc oxide are placed in a three-neck 500 ml round bottom flask equipped with a reflux condenser, addition funnel, heating mantle and magnetic stirrer under gentle agitation. The dropping funnel is charged with about 0.2 moles (44 grams) of the dimethyl ester of azelaic acid), which is added dropwise over the course of about one half hour to the stirred mixture, kept at about 130 degrees centigrade, the methanol liberated being collected in a receiver attached to a side-arm condenser. Following the addition, the temperature of the contents of the flask is maintained for four hours, then cooled to 25 degrees centigrade. The reaction product mixture is next subject to acid hydrolysis in the presence of excess water. The mixture is cooled and the water layer is decanted. 200 milliliters of water are added slowly and the contents mixed gently to enable glycerine present in the mixture to dissolve in the water, without forming large amounts of emulsion, which water is then decanted. This is repeated three times and finally the resulting product mixture, containing a mixture of materials according to formula (I), one wherein R1 is hydrogen and a small amount of one wherein R1 is methyl, and wherein both R2 and R3 are hydrogen in both components, is taken up in ether and washed gently three times more with 100 ml of water to remove the last traces of glycerine. The product is dried (anhyd. magnesium sulfate) and the ether removed, to yield a glyceryl azelates concentrate from which a composition according to the invention may be produced.

EXAMPLE II

Shampoo

One gram of the concentrate produced in Example I is mixed with fifty grams of Alberto VO5® shampoo (Alberto-Culver) in a small cup using a spoon to afford an anti-bacterial shampoo useful for treating the hair and scalp.

EXAMPLE III

Conditioner

One gram of the concentrate produced in Example I is mixed with fifty grams of TRESemme® Pro-Vitamin B5 & Aloe Remoisturizing conditioner (Alberto-Culver) in a small cup using a spoon to afford an anti-bacterial conditioner useful for treating the hair and scalp.

EXAMPLE IV

Skin-Care Composition

One gram of the concentrate produced in Example I is mixed with fifty grams of Fruit of the Earth® Cocoa butter with aloe & vitamin E skin care lotion (Fruit of the Earth, Inc.) in a small cup using a spoon to provide an anti-bacterial skin lotion useful for treating the skin for acne.

EXAMPLE V

Hand and Body Soap

One gram of the concentrate produced in Example I is mixed with fifty grams of Softsoap® hand soap (Colgate-Palmolive) in a small cup using a spoon to provide an anti-microbial soap composition.

EXAMPLE VI

Glyceryl Azelates

One hundred grams of the dried reaction product prepared according to Example I is taken up in 500 ml of toluene and heated to 80 degrees centigrade. A solution of 0.6 moles (130 grams) of lauryl chloride dissolved in 200 ml of toluene is slowly added over the course of two hours, with stirring, maintaining the temperature at 80 degrees centigrade for four hours. The reaction mixture is cooled to room temperature, and mixed with an equal volume of water. After six hours, the water layer is discarded and the residue is treated slowly with one liter of 10% sodium bicarbonate solution, after which the water layer is again discarded. The residue is washed three times with water, dried and the toluene removed under reduced pressure to yield a mixture containing compounds conforming to the structures (II), (III), and (IV) in which R1, R2, R3 are hydrogen, and in which some of the compositions have R1 as being a methyl group. This material can provide compositions according to examples II, III, IV, and V, inter alia.

EXAMPLE VII

Glyceryl Azelates

Example I is repeated, except that glycerine is employed in the place of the glyceryl ketal of acetone previously used as reactant, to afford a crude product mixture comprising glyceryl monoazelate having the azelaic moiety present on both the 1-position and 2-position of the glycerine molecule. The crude product is purified by molecular distillation to separate the compounds corresponding to formulae (I) and (II) from one another. The material corresponding to formula (V) may be treated with the desired molar amount of acid chloride of lauric acid (lauryl chloride) per the procedure of Example VI to yield compounds corresponding to formulae (VI) and (VII), which may be readily worked up and is suitable for providing compositions according to examples II, III, IV, and V, inter alia. These materials may be further purified before use by molecular distillation.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. This includes subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claims so modified. This also includes combination of the features and/or limitations of one or more of the independent claims with features and/or limitations of another independent claims to arrive at a modified independent claim, with the remaining dependent claims in their original text being read and applied to any independent claim so modified. Accordingly, the presently disclosed invention is intended to cover all such modifications and alterations, and is limited only by the scope of the claims which follow.

What is claimed is:

1. A composition of matter useful for topical application to human skin, which comprises at least one ester compound having a structure:

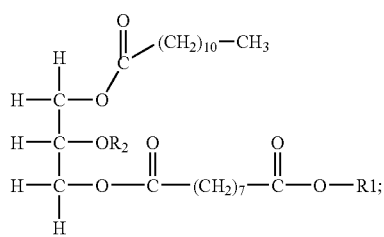
(II)

wherein R1, in each occurrence, is selected from the group consisting of: hydrogen, a metal cation, a substituted or unsubstituted ammonium ion, any C1-C18 hydrocarbyl group, and a glyceryl group having the structure:

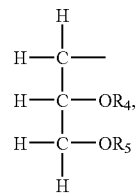

in which R4 and R5 are in each occurrence independently selected from the group consisting of: hydrogen and any C1-C18 hydrocarbyl group; and R2 is selected from the group consisting of: hydrogen, any C1-C18 hydrocarbyl group, and a glyceryl group having the structure:

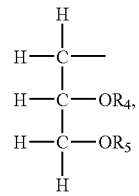

in which R4 and R5 are in each occurrence independently selected from the group consisting of: hydrogen and any C1-C18 hydrocarbyl group.

2. A composition according to claim 1 wherein the total amount of said ester compound(s) present is any amount between about 0.01% by weight to about 80% by weight based on the total weight of said composition.

3. A composition according to claim 1 wherein said at least one ester compound is a compound corresponding to formula (II), wherein R1 and R2 each comprise hydrogen.

4. A composition according to claim 1 wherein said at least one ester compound is a compound corresponding to formula (II), wherein R1 is hydrogen, methyl, or ethyl and R2 comprises hydrogen.

5. A composition according to claim 1 in which R1 is a metal cation selected from the group consisting of: lithium, sodium, potassium, calcium, magnesium, strontium, barium, aluminum, zirconium, and zinc.

6. A composition according to claim 1 in which R1 is a cation selected from the group consisting of: ammonium, monoalkyl ammonium, dialkylammonium, and trialkylammonium.

* * * * *

UNITED STATES PATENT AND TRADEMARK OFFICE
CERTIFICATE OF CORRECTION

PATENT NO. : 7,300,957 B1 Page 1 of 1
APPLICATION NO. : 11/524556
DATED : November 27, 2007
INVENTOR(S) : Christopher J. Whewell It is certified that error appears in the above-identified patent and that said Letters Patent is hereby corrected as shown below:

Title Page;
"(56)            References Cited 4,070,523 A     1/1978  Blum et al. ...................... 428/352
4,542,052 A     9/1985 Shadbolt et al. ................ 428/40
4,661,519 A  *  4/1987 Shiga et al. ..................... 514/547"

should read as follows

-- (56)         References Cited 4,070,523 A     1/1978  Blum et al. ...................... 428/352
4,542,052 A     9/1985 Shadbolt et al. ................ 428/40
4,661,519 A  *  4/1987 Shiga et al. ..................... 514/547
4,847,376 A  *  7/1989 Neumann et al. .............  544/102 --

Signed and Sealed this

Twentieth Day of May, 2008

JON W. DUDAS
*Director of the United States Patent and Trademark Office*